United States Patent [19]

Le Page et al.

[11] 4,197,185

[45] Apr. 8, 1980

[54] PROCESS FOR THE CONVERSION OF OLEFINIC C₄ CUTS FROM STEAM CRACKING TO HIGH OCTANE GASOLINE AND BUTANE

[75] Inventors: Jean-François Le Page, Rueil Malmaison; Jean Cosyns, Maule; Jean Miquel, Paris; Bernard Juguin, Rueil Malmaison, all of France

[73] Assignee: Institut Francais du Petrole, Rueil-Malmaison, France

[21] Appl. No.: 936,965

[22] Filed: Aug. 25, 1978

[30] Foreign Application Priority Data

Oct. 26, 1977 [FR] France .................................. 77 26279

[51] Int. Cl.² .......................... C07C 9/10; C07C 9/20; C10G 57/08
[52] U.S. Cl. ..................................... 208/71; 208/103; 585/310
[58] Field of Search ..................... 208/71, 102, 67, 49, 208/103; 585/310

[56] References Cited

U.S. PATENT DOCUMENTS

| 2,285,785 | 6/1942 | Seguy | 208/71 |
| 2,349,045 | 5/1944 | Layng et al. | 208/103 |
| 3,607,726 | 9/1971 | Hallman | 208/103 |
| 3,654,136 | 4/1972 | Milsom | 208/71 |
| 3,951,780 | 4/1976 | Woo et al. | 208/71 |

*Primary Examiner*—Herbert Levine
*Attorney, Agent, or Firm*—Millen & White

[57] ABSTRACT

Process for producing butane and gasoline of high isooctane content, from a C₄ olefin cut issued from a steam cracking unit, comprising the steps of:
  polymerizing at least 90% of the isobutene of the cut mainly to dimers and trimers thereof,
  hydrogenating the resulting polymerization mixture to normal butane, isooctane and isododecane,
  supplying the effluent from the hydrogenation unit to a separation zone to recover a gaseous fraction and a liquid mixture, and
  fractionating the liquid mixture to separate gasoline of high isooctane content, a C₃⁻ fraction and a butane fraction which is recycled to the steam cracking unit.

11 Claims, 1 Drawing Figure

U.S. Patent  Apr. 8, 1980  4,197,185
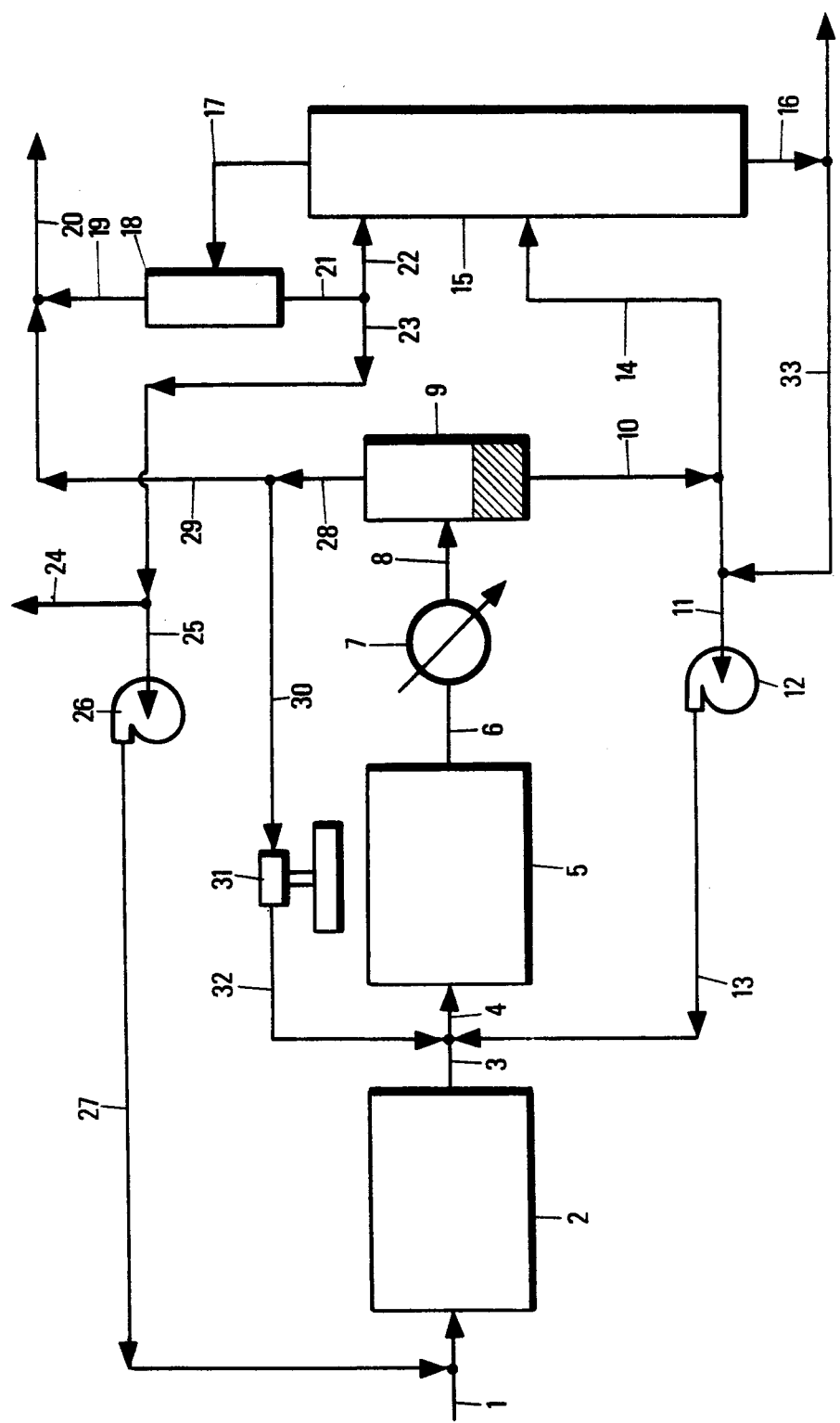

PROCESS FOR THE CONVERSION OF OLEFINIC C₄ CUTS FROM STEAM CRACKING TO HIGH OCTANE GASOLINE AND BUTANE

BACKGROUND OF THE INVENTION

The development of steam cracking units which can be expected in the future will introduce into the market an excess of normal butanes and isobutanes and it will be therefore necessary to find new uses for these materials. As a matter of fact, the increasing demand of ethylene, propylene and benzene will also result in an excess of olefinic C₄ cut as obtained from butadiene extraction plants.

It has already been proposed in the French Pat. No. 1,417,238 (or the Canadian Pat. No. 803,572) to convert C₄ cuts to gasoline by a process wherein the C₄ cut is subjected to polymerization followed with hydrogenation of the resultant polymers. However this process is not selective since, particularly in the course of the polymerization, there are obtained mixtures of isobutene dimers and trimers, pentenes, hexenes and heptenes and, consequently various hydrocarbon mixtures during the hydrogenation step which follows the polymerization.

DETAILED DISCUSSION

It is an object of this invention to provide a selective process for producing butane and gasoline of high isooctane content, from a cut issued from a steam cracking unit and essentially containing hydrocarbons having 4 carbon atoms per molecule and, particularly, isobutene, butenes, butane and isobutane. The process consists, in a first step, of selectively polymerizing isobutene to dimers and trimers, with a minimum conversion of the normal butenes (without substantial conversion of butane or isobutane of the charge: converting less than 10% of isobutane by weight, and less than 2, or better 1%, by weight of butane), then, in a second step, of hydrogenating the mixture obtained after polymerization, to normal butane, isooctane and isododecane. The hydrogenated gasoline fraction has a high value in view of its very high octane number (clear RON≧100) and the obtained normal butane is recycled to steam cracking, with a relatively small amount of isobutane, this being an advantage in view of the fact that mainly normal butane (resulting in high yields of ethylene, propylene and butadiene) and only a low amount of isobutane, is recycled to the steam cracking unit. (It is advisable to avoid the recycling of high isobutane amounts which, while resulting in good propylene yields, gives only low yields of ethylene and high yields of methane, which can be used only for its heating value).

The process corresponding to the invention is diagrammatically illustrated in the accompanying drawing. In a first step, the C₄ cut is fed through line 1 to the polymerization zone 2 under such conditions that isobutene reacts up to conversion rates higher than 90% by weight whereas the total conversion of normal butenes (1-butene and 2-cis- and trans-butenes) remains lower than 10% by weight (or preferably lower than 5% by weight). Resultant gasoline comprises mainly a mixture of isobutene dimers (60 to 80% by weight) and trimers (20 to 40% by weight) the percentages being expressed with respect to said dimer and trimer mixture. The operation is performed under the following operating conditions:

Space velocity (VVH): 0.5 to 5 (in liter of charge per liter of catalyst and per hour).
Pressure: 25 to 60 bars.
Temperature: 100° to 180° C.

In view of a high exothermicity of the transformation it is preferable that the isobutene content of the charge be not in excess of about 35% by weight. Otherwise, it is advantageous to dilute the charge, for example with butane, isobutane or, for example, with a butane fraction recovered from the top of the stabilization column 15, which is recycled to the polymerization step, either at the top of the reactor or between different portions of the catalyst bed so as to avoid too high temperature increase.

The polymerization catalyst is either fluorinated alumina or boron-alumina or, preferably, silica-alumina whose silica content is from 60 to 95% by weight and, preferably, from 70 to 90%. These catalysts are used as balls or extrudates or pills whose equivalent diameter is, for example, from about 2 to 5 mm.

At the outlet of the polymerization unit, all the effluents including unconverted butenes, dimers, trimers and dilution butane, are directly (without intermediate fractionation step and without intermediate cooling other than that which can take place in the transfer lines between the polymerization zone and the hydrogenation zone) fed, through lines 3 and 4, to the hydrogenation step in zone 5. The hydrogenation operating conditions are as follows:

VVH: 1 to 5
Pressure: 25 to 60 bars
Temperature: 150° to 220° C.

In order to avoid a too high temperature increase, as a result of the high exothermicity of the reaction, liquid from the separator drum 9 (and/or from the bottom of the distillation column 15) is recycled to the top of the hydrogenation catalyst bed, through lines 10, 11, 33, pump 12 and line 13. The recycle rate will essentially depend on the olefin content of the product discharged from the polymerization zone 2, through line 3. This olefin content is generally from 30 to 60% by mole and the liquid recycle rate will vary from 5 to 50% by weight. The hydrogen gas used for the hydrogenation may be either pure hydrogen or hydrogen issued from the atom cracking unit or from a catalytic reforming unit. The molar ratio H₂/hydrocarbon, at the inlet of the reactor 5, is from 1 to 4 and preferably from 1.5 to 2.5. At the outlet of the hydrogenation unit, the product is cooled down in zone 7 and fed, through line 8 to separator 9, wherefrom are separated: (a) gas withdrawn through line 28, which is partly recycled through line 30, compressor 31 and line 32, to reactor 5 and, (b) liquid which may also be partly recycled, as above mentioned. The non-recycled liquid fraction is fed, through line 14, to a stabilization column 15 wherefrom is separated a gasoline fraction of very high isooctane content, withdrawn through line 16, which may be used as premium gasoline (a portion thereof, for example up to 15% by weight, may be recycled, through line 33, to the hydrogenation zone 5) and a fraction of high normal butane content, withdrawn through line 17, fed to separator 18 to remove, through lines 19 and 20, the hydrocarbons having 3 or less than 3 carbon atoms per molecule (C₃⁻). There can also be recovered, through line 20, a portion of the C₃⁻ hydrocarbons issued, through lines 29 and 28, from separator 9. The normal butane fraction, generally containing less than 15% by weight of isobutane, issued from separator 18 and withdrawn through line 21, is recycled through lines 23 and 24 to the steam cracking unit. A portion of the butane and the isobutane contained in this fraction may be recycled through line 22 to the distillation or stabilization column 15, another portion may be recycled to the polymerization zone 2 through lines 23 and 25, pump 26 and line 27. In the case where the hydrogen gas is not pure but also contains methane, ethane, propane and butanes, it is recommended to subject the purge gas, discharged through line 28 from separator 9, to a second absorption, not illustrated on the figure, by means of a portion of the product of line 16 at the bottom of the stabilization column. The gasoline charged with butanes and propane from this absorption step is recycled to the stabilization column.

The catalyst used for the hydrogenation may be either a catalyst based on nickel or a catalyst making use of a noble metal or a mixture of noble metals as active agents; in the latter case, palladium or platinum are used preferably. In any case, the hydrogenation catalyst carrier must be a non-acid carrier so as to avoid parasitic polymerization reactions resulting in the formation of gums which clog the catalyst. Among the carriers which can be used, according to the invention, are silica, kieselguhr (hydrated silica), aluminas of low specific surface (less than 100 m²/g and particularly from 10 to 90 m²/g), and the nickel or cobalt aluminates prepared, for example, from cubic γ alumina containing 5 to 10% of nickel or cobalt oxides introduced, for example, as nitrates, the so-impregnated carrier being then roasted at a temperature from 800° to 900° C.

EXAMPLE 1

This example relates to the treatment of a charge obtained by dilution of a C₄ steam cracking cut with a mixture of butane and isobutane; the composition of the so-obtained charge No. 1 is given in Table I below. Charge No. 1 is treated in two serially arranged fixed bed reactors; between the two reactors (the first reactor being a polymerization reactor and the second one a hydrogenation reactor), a a device provides the supply of hydrogen required for the hydrogenation reaction as well as the liquid recycle used for avoiding too high temperature increase in the hydrogenation reactor. Each of the reactors is operated under substantially isothermal conditions. Catalyst K₁, used in the first reactor (polymerization), is silica-alumina available in the trade, of the type called Durabead Perl Catalysator Neu from Kalichemie Society. Catalyst K₁' used in the second reactor (hydrogenation reactor), is a catalyst containing 0.3% of Pd (by weight) deposited on alumina having a specific surface of 60 m².g⁻¹ and a pore volume of 0.5 cc.g⁻¹. The operating conditions in each of said reactors are reported in Table II; 20% of the gaseous fraction obtained in the separation zone where is supplied the effluent from the hydrogenation zone, are recycled to said hydrogenation zone.

TABLE I

| Composition of the charge (% by weight) DILUTED CHARGE No. 1 OF EXAMPLE 1 | |
|---|---|
| Propane | 1.6 |
| Isobutane | 3.9 |
| Butane | 28.1 |
| Isobutene | 35.5 |
| 1-butene | 18.5 |
| Trans 2-butene | 7.5 |
| Cis 2-butene | 4.5 |
| Butadiene | 0.4 |

TABLE I-continued

| Composition of the charge (% by weight) DILUTED CHARGE No. 1 OF EXAMPLE 1 | |
|---|---|
| Isopentane | traces |
| Pentenes | traces |

TABLE II

| Operating conditions | POLYMERIZATION | HYDROGENATION |
|---|---|---|
| VVH (in h⁻¹) | 2 | 1.5 on fresh diluted charge (initial) |
| T °C. | 150 | 200 |
| P bars | 40 | 40 |
| H²/HC (moles) | — | 1 on fresh diluted charge (initial) |
| Liquid recycle rate | — | 6 |

Table III gives the composition of the products obtained respectively at the end of the 24th hour of test and at the end of the 240th hour of test, at the outlet of the polymerization unit (products C₁ and C₂) and at the outlet of the hydrogenation unit (products D₁ and D₂). (For analyzing the polymerizate before hydrogenation, the temperature of the hydrogenation reactor is lowered to room temperature (≠20° C.) and the hydrogen supply is discontinued. The composition of the product as well in the liquid phase as in the vapor phase is then determined.) It is observed that, during polymerization, isobutene selectively oligomerizes and the normal butenes react very slowly to form polymers or copolymers.

TABLE III

| COMPOSITION % by weight | 24 HOURS | | 240 HOURS | |
|---|---|---|---|---|
| | C₁ | D₁ | C₂ | D₂ |
| Propane | 1.6 | 1.6 | 1.6 | 1.6 |
| Isobutane | 3.7 | 6.6 | 3.7 | 7.0 |
| Butane | 28.1 | 57.2 | 28.1 | 58.2 |
| Isobutene | 2.8 | — | 3.3 | — |
| 1-Butene | 9.0 | — | 10.1 | — |
| Trans 2-Butene | 12.1 | — | 13.2 | — |
| Cis 2-Butene | 7.9 | — | 6.8 | — |
| Butadiene | traces | — | traces | — |
| C₈ Olefins (Isobutene dimers) | 25.8 | 1.8 | 25.1 | 1.9 |
| C₁₂ Olefins (Isobutene trimers) | 9 | 1.0 | 8.1 | 1.3 |
| C₅⁺ Paraffins | traces | 32 | traces | 30.0* |

*Containing by weight, 92% isooctane, 7.5% isododecane and 0.5% miscellaneous.

The C₅⁺ paraffin fraction is recovered as gasoline. However 5% by weight of said fraction is recycled to the hydrogenation zone.

5% by weight of the mixture of the butane fraction with the isobutane fraction is recycled to the fractionation zone 15; 8% of said mixture of the butane fraction with the isobutane fraction is fed back to the polymerization zone for diluting the charge. The remainder of the mixture of the butane fraction with the isobutane fraction is fed to the steam cracking unit from which originated the charge treated according to the invention.

EXAMPLE 2

The diluted charge No. 1 is treated in the same apparatus as that described in example 1 but with catalysts of different formulas: the polymerization catalyst is still silica-alumina, but prepared according to the following method: 137 g of alumina hydrate Al(OH)$_3$ is suspended into 2.3 kg of a limpid solution of colloidal silica containing 30% of SiO$_2$. Silica is then precipitated by acidifying the solution with nitric acid. Silica precipitates as a gel covering the particles of the aluminum hydrate initially added to the solution. The resulting gel is dried at 120° C. and then extruded. The resulting extrudates are then roasted at 600° C. for 4 hours; the surface of the resulting catalyst is 327 m$^2$.g$^{-1}$ for a pore volume of 0.47 cc.g$^{-1}$ and its alumina content is 24% by weight (catalyst K$_2$).

The hydrogenation catalyst is a catalyst based on prereduced nickel containing 42% by weight of nickel deposited on Kieselguhr and used as pills of 4 mm diameter (catalyst K$_2$'). The catalyst is reduced at 210° C. under hydrogen stream before use. The other operating conditions as well for polymerization as for hydrogenation, are the same as in example 1. The results are reported in Table IV. Various recyclings are performed as indicated in example 1 and to the same extent.

TABLE IV

| COMPOSITION | 48 HOURS | | 288 HOURS | |
|---|---|---|---|---|
| % by weight | C$_3$ | D$_3$ | C$_4$ | D$_4$ |
| Propane | 1.6 | 1.6 | 1.6 | 1.6 |
| Isobutane | 3.6 | 4.7 | 3.7 | 6.9 |
| Butane | 28.1 | 56.2 | 28.1 | 57.9 |
| Isobutene | 1.1 | — | 3.2 | — |
| Total normal butenes | 28.1 | — | 29.8 | — |
| Butadiene | traces | — | — | — |
| C$_8$ Olefins (Isobutene dimers) | 28.1 | 0.4 | 25.4 | 0.6 |
| C$_{12}$ Olefins (Isobutene trimers) | 9.4 | 0.5 | 8.0 | 0.7 |
| C$_5$+ Paraffins | traces | 36.6 | traces | 32.3* |

*containing, by weight, 91% isooctane, 8.4% isododecane and 0.6% miscellaneous.

EXAMPLE 3

The diluted charge No. 1 is treated under the same operating conditions and with the same apparatus as in example 1 but with catalyst of different formulas.

There is used, for three different tests, three polymerization catalysts based on fluorinated alumina which has been prepared by impregnating cubic γ alumina with a solution of a fluorinated compound, respectively hydrofluoric acid, borohydrofluoric acid and ammonium fluoride. The catalyst is then roasted at 550° C. The fluorine content of the final catalyst is 5% by weight. It will be made apparent herebelow that for the production of isooctane, the obtained catalysts are slightly less active than the catalysts based on silica alumina as in examples 1 and 2 and the polymerization operation, in this case, is conducted at a VVH=1 instead of VVH=2, the other operating conditions being the same as those indicated in Table II.

The hydrogenation is performed over the same catalyst as that of example 1 (K$_1$') and under the same operating conditions. The results are summarized in Table V. Three polymerization catalysts have been used, which differ from each other by the use of a different fluorinated precursor for depositing fluorine, i.e. HF (K$_3$ catalyst), BF$_4$H (K$_4$ catalyst) and NH$_4$F (K$_5$ catalyst).

TABLE V

| COMPOSITION OF THE PRODUCT AFTER HYDROGENATION (% by weight) | K$_3$ + K$_1$' (48 hours) | K$_4$ + K$_1$' (48 hours) | K$_5$ + K$_1$' (48 hours) |
|---|---|---|---|
| Propane | 1.6 | 1.6 | 1.6 |
| Isobutane | 4.7 | 7.3 | 5.4 |
| Butane | 56.2 | 58.2 | 57.9 |
| Olefins - C$_5$+ paraffins | 29.5* | 26.1** | 27.7*** |

*containing 90% of isooctane and 8% of isododecane
**containing 90.5% of isooctane and 6.8% of isododecane
***containing 90.5% of isooctane and 7.4% of isododecane.

What we claim is:

1. A process for producing butane and gasoline of high isooctane content which comprises the steps of:
    (a) contacting an olefin cut consisting essentially of hydrocarbons having 4 carbon atoms per molecule, originating from a steam cracking unit, and optionally diluted with a mixture of butane and isobutane as hereinafter defined, in a catalytic polymerization zone with a catalyst selected from the fluorinated aluminas, the boron-aluminas and the silica-aluminas, whereby at least 90% of the isobutene of the cut is converted mainly to isobutene dimers and trimers, and less than 10% by weight of the normal butenes of the cut are polymerized, the butane and the isobutane contained in the olefin cut being substantially unconverted;
    (b) passing the effluent from the polymerization zone, without any intermediary fractionation, to a catalytic hydrogenation zone, and hydrogenating the effluent;
    (c) passing the effluent from the hydrogenation zone to a separation zone wherefrom is withdrawn a gaseous fraction at least one portion of which is recycled to said hydrogenation zone, and a liquid fraction;
    (d) fractionating at least a portion of said liquid fraction in a fractionation zone wherefrom is withdrawn (i) a gasoline fraction of high isooctane content, and (ii) a fraction consisting essentially of hydrocarbons having 4 or less than 4 carbon atoms per molecule;
    (e) separating said fraction (ii) in a separation zone wherefrom is withdrawn a hydrogen fraction containing 3 or less than 3 carbon atoms per molecule; and a mixture consisting essentially of butane and isobutane, the proportion of isobutane being less than 15% by weight; and
    (f) recycling at least a portion of said mixture consisting essentially of butane and isobutane, recovered from step (e), to the steam cracking unit, a portion of said mixture optionally being used to dilute the olefin cut supplied to step (a).

2. A process according to claim 1, wherein an olefin cut containing more than about 35% by weight of isobutene is diluted with at least a portion of said mixture consisting essentially of butane and isobutane recovered from step (e), and the diluted cut is supplied as the charge to step (a).

3. A process according to claim 1, wherein at least a portion of the liquid fraction obtained in step (c) is recycled to the hydrogenation zone.

4. A process according to claim 1, wherein the polymerization catalyst in step (a) is silica-alumina whose silica content is from 60 to 95% by weight.

5. A process according to claim 2, wherein the recycled fraction of said mixture consisting essentially of butane and isobutane used to dilute the olefin cut amounts to 5 to 10% by weight of the resultant charge.

6. A process according to claim 1, wherein the hydrogenation catalyst carrier is selected from silica, kieselguhr, aluminas of a specific surface lower than 100 m$^2$/g and nickel or cobalt aluminates.

7. A process according to claim 4 wherein the silica content is from 70 to 90% by weight.

8. A process according to claim 1, wherein at least a portion of said gasoline fraction (i) obtained in step (d) is recycled to the hydrogenation zone.

9. A process according to claim 8, wherein at least a portion of the liquid fraction obtained in step (c) is also recycled to the hydrogenation zone.

10. A process according to claim 1, wherein the polymerization step (a) is effected at a space velocity of from 0.5 to 5 h$^{-1}$, a pressure of from 25 to 60 bars and a temperature of from 100° to 180° C.

11. A process according to claim 1, wherein the hydrogenation step (b) is effected at a space velocity of from 1 to 5 h$^{-1}$, a pressure of from 25 to 60 bars and a temperature of from 150° to 220° C.

* * * * *